Figure 1:
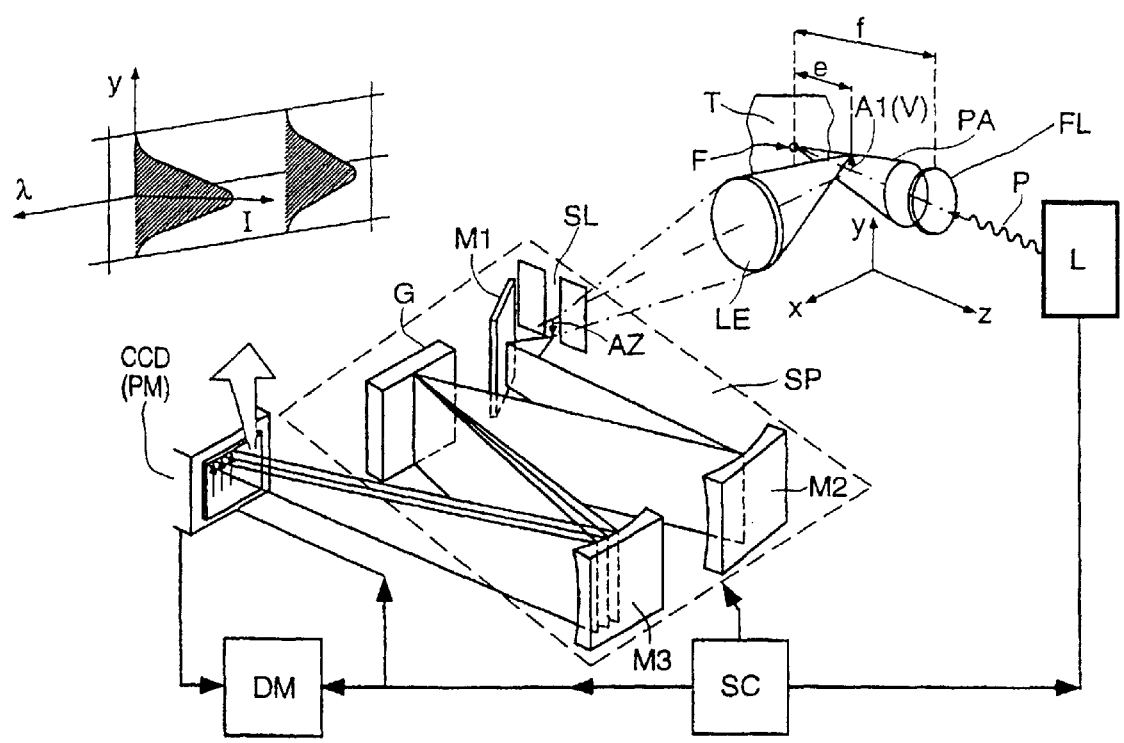

United States Patent
Rohr et al.

[19]

[11] Patent Number: 6,069,695
[45] Date of Patent: May 30, 2000

[54] PROCESS AND ARRANGEMENT FOR LASER-INDUCED SPECTRAL ANALYSIS

[75] Inventors: Klaus Rohr, Kaiserslautern; Jochen Eicher, Wachenheim; Norbert Müller, Friedelsheim, all of Germany

[73] Assignee: EMTEC Magnetics GmbH, Ludwigshafen, Germany

[21] Appl. No.: 09/194,590

[22] PCT Filed: Jun. 26, 1997

[86] PCT No.: PCT/EP97/03360

§ 371 Date: Nov. 30, 1998

§ 102(e) Date: Nov. 30, 1998

[87] PCT Pub. No.: WO98/00702

PCT Pub. Date: Jan. 8, 1998

[30] Foreign Application Priority Data

Jul. 1, 1996 [DE] Germany ............... 196 26 320

[51] Int. Cl.[7] ............... G01J 3/30; G01J 3/443
[52] U.S. Cl. ............... 356/318; 356/316
[58] Field of Search ............... 356/316, 318, 356/317; G01J 3/30, 3/443

[56] References Cited

U.S. PATENT DOCUMENTS

| | | | |
|---|---|---|---|
| 3,597,086 | 8/1971 | Mela | 356/318 |
| 4,687,539 | 8/1987 | Burns et al. | 216/60 |
| 5,446,538 | 8/1995 | Noll | 356/318 |
| 5,715,053 | 2/1998 | Loge | 356/318 |
| 5,798,832 | 8/1998 | Hnilica et al. | 356/316 |

FOREIGN PATENT DOCUMENTS 43 41 462  6/1995  Germany .

OTHER PUBLICATIONS

Applied Spectroscopy, 47 (1993), No. 10, Zuzuya et al. 1659–1664.

*Primary Examiner*—Frank G. Font
*Assistant Examiner*—Layla Lauchman
*Attorney, Agent, or Firm*—Keil & Weinkauf

[57] ABSTRACT

A pulsed laser is employed for quantitative spectral analysis of halogen-containing, nonmetallic or at most partially metallic materials in combination with an image recorder, a spectrometer and a CCD camera, by detecting, summing and analysing the luminous intensity of at least a volume slice from the expansion cone of the plasma, this making it possible, advantageously, for temperature and density gradients to be measured.

23 Claims, 3 Drawing Sheets

PROCESS AND ARRANGEMENT FOR LASER-INDUCED SPECTRAL ANALYSIS

The invention relates to methods and arrangements for spectral analysis by means of laser emission of non-metallic or at most partially metallic materials containing halogen, in particular chlorine, a pulsed laser beam being directed at the material to generate a plasma and the light emitted by the plasma in an expansion direction in conical form being focused optically, being passed to a spectrometer and being analyzed after a predefined delay after the laser beam has been triggered, and the pulsed laser beam having an energy density between about $10^8$ and about $10^{12}$ W/cm$^2$.

Such a method and an arrangement for this purpose have previously been disclosed, for example by EP-B-176 625, for the spectral analysis of steel, where the light emitted by a quasi-pointlike plasma volume is detected one-dimensionally via a photofilm, a photodiode or a photomultiplier tube and is then evaluated for analysis. This known method requires inert gas to be introduced to improve the accuracy of the analysis results. Method and arrangement are unsuitable for the spectral analysis of halogens.

In principle, spectral analysis is based on the fact that the intensity of the spectral lines is proportional to the density $n_i$ of the emitting atom of the materials in state i and the Boltzmann factor $e^{-E_i/kT}$, where $E_i$ is the excitation energy and T is the temperature. In a gas or plasma of constant density and temperature this provides, in a simple manner, the option even of quantitative analysis. In the plasma generated by a pulsed laser beam the situation is considerably more complicated, since the plasma has large gradients both in density and in temperature over time as well as over space, and is therefore not homogeneous, the gradients depending not only on the generating conditions but also on the individual materials.

It is therefore an object of the present invention to improve, in the abovementioned respect, the methods and arrangements for laser-induced spectral analysis of nonmetallic and at most partially metallic materials containing halogen, in particular chlorine.

This object is achieve by means of the method of the type mentioned at the outset, by means of averaging being carried out temporally and spatially over a range of density gradients and temperature gradients of the plasma in order to obtain stable, reproducible spectral line information for analysis, by means of all of the luminous intensities emanating from at least one volume slice of the expansion cone being summed and averaged.

Since this procedure takes place in a short, temporally predefined time during which the temperature of the dilute plasma remains sufficiently high, as does, consequently, the specific light emission of chlorine, it is possible to use all of a large plasma volume, especially for the purposes of quantitative spectral analysis.

A reliable and reproducible, relatively simple, rapid and flexible detection of halogens and in particular of chlorine in compositions of materials is a special advantage of the present method and the corresponding arrangement.

The main reason that laser-induced spectral analysis of chlorine has hitherto not been successful is that the excited states of the halogen atoms are at very high energy, at about 10 eV. In accordance with the Boltzmann factor, strong emissions therefore occur only in the region of the hot plasma focus having temperatures of about $10^{5\circ}$ K. In this region, however, the electron density of the plasma is very high, so that the line emission is completely dominated by the intense bremsstrahlung of identical wavelength of the electrons present there in high density, an analysis thus being prevented. Since the resonance transitions for halogens, moreover, are consequently in the wavelength range of typically 100 nm, they can be detected only by means of the considerably less convenient VUV spectroscopy. (VUV= vacuum ultra violet region 1<250 nm).

It is an advantage of the method that the volume slice (in the form of a conical section or angled) can be generated by a single laser shot and, surprisingly, is sufficient for spectral analysis. In a further refinement of the method, the volume slice is projected across the entrance slit of the spectrometer and is dispersed spectrally, and the spectrum of the volume slice is detected two-dimensionally by a matrix-type image recording system. Another advantage is provided if the matrix-type image recorder used is a CCD camera comprising a chip having at least 10 rows. Thus, as many contributions to a wavelength as possible can be utilized by summing the information of the respective luminous intensities in the corresponding row or column of the image recorder or of the CCD chip, respectively.

This offers the advantages a), that in contrast to customary storage at most row by row (e.g. by a line scan camera), a gain in intensity according to the number of summed rows or columns n is achieved, and b), that a simultaneous improvement in the statistics according to $n^{1/2}$ (square root of n) results.

This likewise permits shorter analysis times. If n=500, the improvement in statistics is by about a factor of 22, for n=2000, however, by as much as a factor of 44, ie. twice as much. A 500-row CCD standard camera is sufficient for practical purposes, however.

It has proved to be surprisingly beneficial to employ a finite, sufficiently large volume slice of the expansion cone for analysis. This results in the option of spatial and temporal averaging over the light emission of the entire inhomogeneous plasma density range and plasma temperature range located therein. Consequently, the analytical procedure becomes relatively noncritical with respect to the ever-present fluctuations between shots, of the plasma density distribution and plasma temperature distribution, for example when switching to different materials and/or carrying out observations in different additional spectral regions. The volume slice itself in this case, in terms of its longitudinal extent (defined by the longitudinal direction of the spectrometer slit) can be oriented in the expansion direction, but is preferably oriented perpendicularly to the expansion direction. Compared with short-range averaging, as carried out even in analyses using line scan cameras, the gain in the present case is about two orders of magnitude (typically defined by the ratio of the height of the spectrometer slit to its width=5 mm/0.01 mm=500). The mean focal distance between the material be analyzed and the volume slice may be about 3 to 6 mm for chlorine analysis.

Serial detection of the intensity values of a plurality of plasmas is possible via a plurality of volume slices with successive laser shots.

In a further refinement of the method, the pulsed laser beam should have a Gaussian distribution, which can advantageously be generated by a laser operated in TEM$_{00}$ mode. Such lasers have particular stability in terms of energy and beam shape, so that high reproducibility between shots is achieved in the focal region and also in the plasma.

The predefined delay should expediently be 4 ms for chlorine analysis at the said focal distances, since at that time with respect to the generation of the plasma the bremsstrahlung is no longer a problem and at the same time the emission intensity of the chlorine line important for the analysis, at about 838 nm, is at a maximum.

Expediently, the luminous intensity can be analyzed during a time window of at least 100 ns after the predefined delay has elapsed.

The time window of the image acquisition system (amplifier-timeswitch-recorder) should be optimizable via an electronic control system, in conjunction with an image intensifier, with a temporal resolution in the 10 ns range, in accordance with the spectral lines to be analyzed. The optimization depends on the laser-object relationships (type of laser, material to be analyzed), the position of the particular characteristic spectral line and the focal distance of the volume to be studied. In a practical design, the matrix-type image recorder may be a CCD camera comprising a chip having at least 10 rows. More useful and cheaper are standard cameras (from about 500 to about 600 rows and columns), although a special camera having more rows and, in particular, more columns, e.g. 2000, would be even more useful for the measuring procedure.

Likewise, it is expedient for the digital memory logic and analysis logic connected downstream of the matrix-type image recording system to have a memory depth of at least 4 bits and at least about 15×15 memory locations. A higher memory depth of from about 8 to 12 bits, and a number of memory locations appropriately tailored to the image acquisition system would be desirable.

As a further improvement of the method it is beneficial for the plasma produced to be specifically postexcited by means of an additional electrical discharge and the light emitted thereupon, as described, being passed to the spectrometer.

Thus the sensitivity of halogen detection, in particular of chlorine detection, can be raised by about a factor of 10. This results in a detection limit for chlorine, e.g. in the arrangement described, of less than 1%, even down to 0.5%.

In an expedient refinement of the method, chlorine analysis makes use of the spectral lines in the region from about 480 nm to about 550 nm, or at 837.594 nm or at 858.597 nm.

Thus, advantageously, strong lines are used which are within the spectral range or at least in the range which can be covered by optical components made of glass, of from about 300 nm to 3000 nm, and preferably in the visible range or the near infrared and which are not masked by other strong lines of the remaining constituents (e.g., H, O, N, C of nonmetallic materials). Very useful, it was found, is the line in the near infrared (IR) region at 837.594 nm (about 838 nm), although the other lines in the region between about 480 and 550 nm and at 858.597 nm (approximately 859 nm) likewise gave good analytical results.

The method according to the invention illustrated hereinabove with reference to the patent claims can advantageously be carried out using arrangements according to the invention having the following distinguishing features:

The arrangement comprises a pulsed laser which, in particular, is operated in the $TEM_{00}$ mode and whose pulsed laser beam having an energy density between about $10^8$ and about $10^{12}$ W/cm$^2$, is directed at the nonmetallic or partially metallic material, an optically focusing means, which directs and collimates the light emitted by the plasma to the slit of a spectrometer, a matrix-type image recorder by means of which the intensity of the volume slice, projected via the spectrometer slit, of the emitted light after it has passed through the spectrometer is spectrally resolved and can be summed, temporally and spatially, by means of an image storage device and analysis device, and a control device between the laser, the spectrometer, the image recorder and the analysis device, for correct storage and analysis, in terms of time intervals, of the spectral signals of the emitted light.

The image memory devices and analysis devices advantageously comprise digital logic units and are situated downstream of the image recorder. This provides an advantageous arrangement comprising a highly suitable, pulsed laser type, e.g. a Q-switched or mode-locked Nd-YAG laser, a simple optically focusing means and a timing device is provided, the latter, after the laser pulse has been triggered, controlling the predefined delay between individual analyses, the time window of the image recording system, image memory system and analysis system and thus recording of the spectral signals and even their digital storage and analysis, before the next laser pulse can be triggered. This results in optimal time management of the analysis arrangement.

In a practical advantageous embodiment, the matrix-type image memory is a CCD camera having at least 10, in particular from about 500 to about 600 rows (horizontal and vertical sensor locations).

To generate the time window it is advantageous for an image intensifier to be connected upstream of the image memory. The spectrometer may expediently include image field-correcting elements (flat-field units).

An improvement in the detection sensitivity of the method and the arrangement is achieved by means of a postexcitation device which may expediently comprise a triggered spark gap having Cu electrodes, a voltage of about 5 kV and a capacitance of about 2 mF and an inductance of about 100 mH, for a spark energy of about 25 Ws. Thus detection of chlorine down to a percentage by volume of about 0.5% becomes possible.

Further features beneficial in practice are long-focus focusing of the laser beam onto the target in order to achieve, on the one hand, a long working distance and, on the other hand, a beam shape having a large Rayleigh length. As a result, unevennesses on the object to be analyzed are less critical. Moreover, unless microanalysis is being aimed for, a large focal spot having a diameter of about 0.1 mm to about 1 mm is beneficial, since this means that any differences on the object are averaged out and more extensive one-dimensional (in the normal orientation of the object) expansion of the plasma with consequent improved analysis possibilities is achieved.

The detection of halogen depends crucially on a high plasma temperature. Beneficial for a high plasma temperature is a high absorption of the incoming laser light in the material to be analyzed and in the expanding plasma. This can be achieved by employing as short as possible a wavelength of the laser, e.g. the frequency-quadrupled Nd-YAG fundamental wavelength of 1.06 mm up to the ultraviolet, e.g. 250 nm. A controlled increase in the initial absorption (particularly for a long laser pulse, e.g. in the ns range) is beneficial by means of controlled, thin coating of the object with a material which strongly absorbs the wavelength used of the laser, but does not interfere with the analysis, e.g. graphite.

Figure 2:
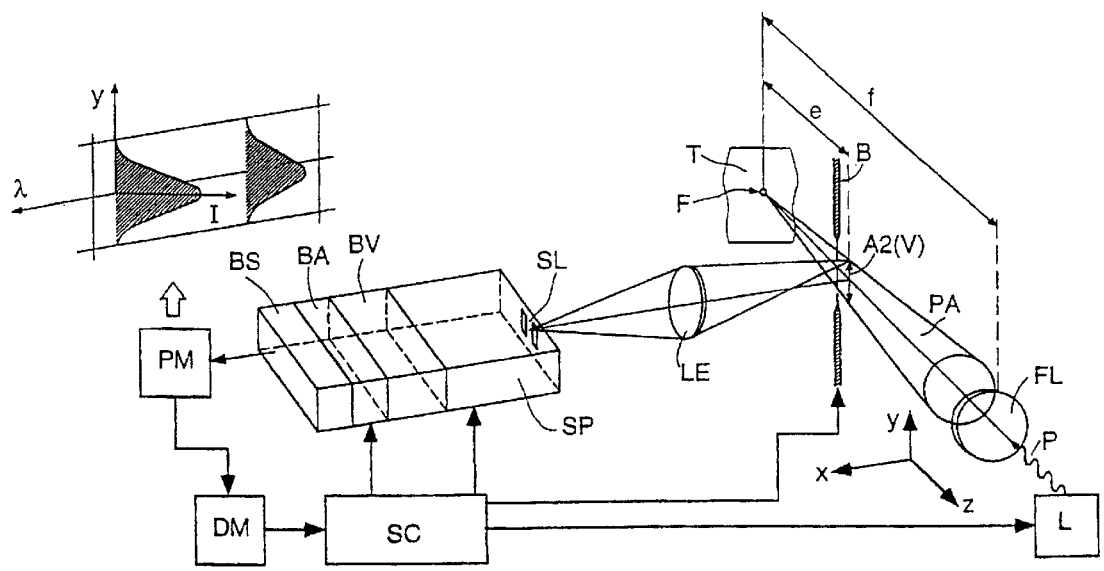
Figure 3:
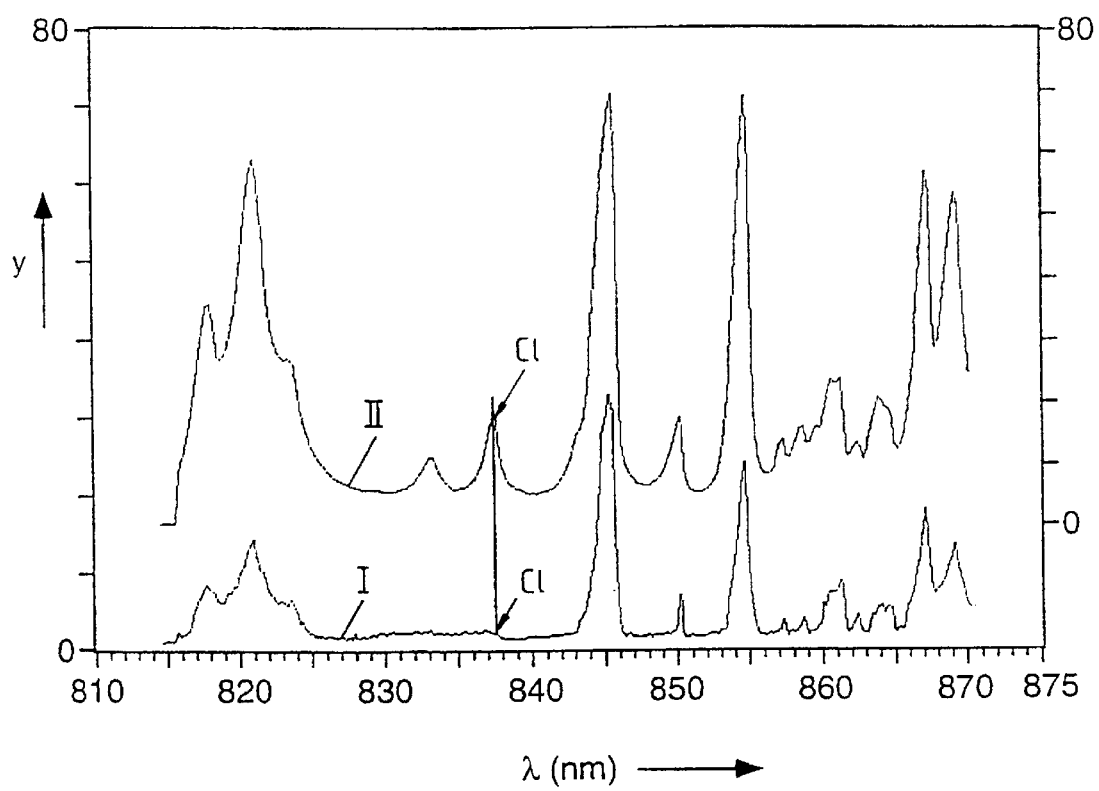

An arrangement according to the invention is described hereinafter by way of example with reference to the schematic shown in FIGS. 1 and 2 of the drawing, and examples of analysis spectral lines are shown in FIG. 3.

The laser L is caused, via the control unit SC, to emit a laser pulse P. The laser pulse P is focused, via optics FL, onto the nonmetallic or at most partially metallic material T to be analyzed and there generates a plasma PA, which expands, e.g. in the form of an expansion cone. In the direction toward a spectrometer SP there are imaging achromatic optics LE, which form an image of the volume slice V of the plasma at the mean distance e from object T on the entrance slit SL of the spectrometer SP. In the process, the longitudinal direction of the slit determines the orientation of the selected volume slice (y or z direction) of the plasma region of which an image is to be formed. In FIGS. 1 and 2, a direction perpendicular to the principal expansion direction of the plasma (y direction) has been drawn. The longitudinal extent of the slit SL (typically 5 mm), together with the imaging optics (LE), define the slice diameter of the volume slice under consideration, whereas the variable slit width (typically about 10 mm) determines the thickness of the volume slice and, in particular, the spectral resolution. Therefore, the slit width SL can be freely chosen only within the scope of the resolution required (typically a few nm in the worst case) for increasing the luminous intensity. The options of nevertheless changing the size of the volume slice element by enlarging it in its longitudinal direction, of freely choosing its orientation, and using it for analysis in its entirety or in part essentially form the basis for the present distinguishing features of the method and the arrangement.

Via the optics LE, an image of the volume slice V of the plasma cone PA is formed on the slit SW of the spectrometer SP and is subsequently dispersed spectrally.

The principle and the direction of the addition of the intensity gradients are symbolized by the arrows A1 and A2, for the case, as shown, of the slit being oriented in the y direction.

The purpose of the arrangement is to carry out routine studies of halogen-containing materials in a normal atmosphere and without a laboratory-specific effort. The components of the arrangements described in FIGS. 1 and 2 were selected with this purpose in mind.

The spectrometer SP used is a single-grating monochromator f/4.0 having a 600 L/mm grating and mirrors M1 and M2, M3 and a suitable blaze wavelength of 500 nm. Using a ½" image recorder BA (CCD) it is thus possible to utilize a spectral range of about 60 nm in the focal plane. With the aid of the variable entrance slit SL, the luminous intensity is optimized as far as permitted by the resolution. The slit height is set in accordance with the linear magnification and the longitudinal extent of the plasma volume to be studied (typically 5–10 mm). The spectral information in the image plane of the spectrometer SP can be checked, immediately before further processing, at the output of the image memory BS downstream of the image recording system BA on a monitor PM, and can thus be easily optimized, e.g. in the alignment phase. In FIGS. 1 and 2 this is shown schematically in the subsidiary diagram for two spectral lines, the intensity I being visualizable as a grayscale image, in false colors or as a pseudo-3D image. The image recorder BA used for the picture should, if possible, have a large dynamic range (about 1000) and a wide usable spectral range. Of practical utility is a CCD camera having at least 10 rows, but expediently, as in the present case, a standard camera having an, e.g., 752×582 (columns times rows) chip. The memory depth should in this case be at least 4 bits and, in the present equipment, was 8 bits, although it is advisable to aim for at least 10 bits.

The spectral information contained in the longitudinal direction of the volume slice, this being the y direction in FIGS. 1 and 2, are summed individually for each wavelength in the downstream analysis unit DM and are usually made available as a spectrum in accordance with FIG. 3 for further automated decision. The size and the orientation of the portion (shown in the y direction in FIGS. 1 and 2) of the volume slice V to be used for the analysis can be adjusted optimally, e.g. be programmed, in the analysis unit DM. In the simplest case this purpose is served by a microprocessor or personal computer. The same applies to the control unit SC, which is in charge of the entire control of the arrangement, especially of driving the laser to trigger further pulses, of triggering the spark gap B (in FIG. 2) and the image recording system BA, of the selection, by means of a motor, of the spectrometer wavelength, and of the activation of the analysis unit DM.

In principle, any system can be used as a laser, if its output is sufficiently high to be able to achieve a focal intensity required to evaporate the material and generate the plasma (about $10^8$ to $10^{12}$ W/cm$^2$). A simple option is provided by a Q-switched Nd-YAG laser having pulse durations in the ns range at the fundamental wavelength of 1.06 mm. On the grounds of reproducibility, said laser should preferably operate in the TEM$_{00}$ mode. Advantageously, the plasma temperature, and thus the spectral-line intensity, is increased by frequency-doubling into the green region (530 nm) or even further frequency multiplication as far as into the UV region (e.g. 265 nm). The situation is similar, for the brief Q-switched pulse used, having a duration of 4 ns. A further improvement is achieved by using an even shorter pulse, for example that of a mode-locked laser having pulse durations in the 10 ps range. In the case of long pulses, a specific coating, not interfering with the analysis, of the object (e.g. with graphite) is beneficial so as to increase the initial absorption before plasma is formed.

In a practical advantageous embodiment the optics LE which form an image of the plasma on the spectrometer slit comprise an achromat. The linear magnification, working distance and focal length together with the resolution and entrance slit width of the spectrometer are chosen in such a way that the plasma volume to be analyzed and the spectral window can be optimized. The matrix-type image recording system tailored to the latter expediently comprises a CCD camera having at least 10, in particular from about 500 to about 600 rows (horizontal sensor locations) and from about 500 to about 600 columns (vertical sensor locations). In a practically advantageous embodiment, the image recording system (BA, BS, BV) comprises an electron-optical, spectrally broad band, low-aberration, two-dimensional image intensifier unit BV, which is provided with gate time control at a resolution in the ns range for optional generation of a time window for the picture and whose gain can be controlled, and an integrated image recorder (BA)(CCD camera).

In a practically advantageous and simplified embodiment, the image recording means (photocathode of the image intensifier or, in the case of operation without one, the CCD chip of the camera) is situated directly in the image plane of the spectrometer, without further imaging optics being interposed. The spectrometer may expediently comprise image field-correcting elements (flat-field image plane), not shown.

In the case of chlorine detection for PVC material via the line at 837.6 nm, and with a laser intensity used of about $10^{11}$ W/cm$^2$, a wavelength of 530 nm and a focal distance e of 4 mm, and in the longitudinal direction of the volume slice in the y direction, the optimum value for the delay was 4 ms and for the time window of the image recording system 100 ns. The variable focal distance e itself, which can be between about 3 and about 6 mm, and the delay are chosen in such a way, however, that the degree of excitation at the position of the volume slice (arrow A1) is as high as possible, but that the bremsstrahlung continuum does not significantly impede recording of the lines. Optimization of the focal distance, the delay and the time window is necessary in each case with respect to the laser-object conditions (e.g. laser output, surface of the object, etc).

Focusing of the laser beam is assisted by long-focus optics FL; in the present case, the focal length f=200 mm.

Thus, on the one hand, a favorable working distance is achieved, and on the other hand the effect of the large Rayleigh length is that the reproducibility of the individual plasma pulses is considerably increased. Moreover, the concomitant large diameter of the focus F has the effect that averaging takes place over a certain area of the object. Owing to the expansion geometry which in this case tends to be planar, the density in the expanding plasma PA remains high for longer, and the radial gradients are less.

To increase the analytical sensitivity, e.g. so as to be able to detect even fractions of a percent by volume of chlorine or the other halogens, in certain cases postexcitation of the plasma during expansion is required, as depicted schematically in FIG. 2 by means of a spark gap B. The spark gap B comprises, e.g., copper (Cu) electrodes, between the tips of which a voltage U of up to 5 kV is applied. The discharge energy of up to about 25 Ws is fed from a capacitance of about 2 mF. The purpose of pulse shaping is served by an inductance of about 100 mH. The additional cross-excitation (perpendicular to the expansion direction of the plasma PA) in the region in front of the material T additionally enhances ionization and excitation of the particles in the plasma PA, so that the quantity of light radiated by the plasma is considerably increased, even at the location of the volume slice A2, and improved detectability for the small amounts of halogen, especially chlorine, to be analyzed is thus achieved. In the process, the focal distance e and the time window have to be readjusted empirically.

FIG. 3 shows, in an analysis diagram I=f(l), a comparison which illustrates the advantage of the method used here compared with conventional line-scan spectroscopy. The two curves in FIG. 3 were produced under identical conditions in terms of laser-object interaction and detection (material (PVC), nature of the surface, focal distance, laser intensity, spectral range, spectral (apparatus) resolution, etc.). In the upper spectrum averaging was carried out across the entire cone cross section of the expanding plasma, an image of said cross section having been formed over about 500 lines of the camera. In addition to other substituents of PVC, the isolated chlorine line CL at 837.6 nm is clearly visible. In the bottom spectrum a line-scan camera was simulated by averaging carried out across only 20 lines of the camera. This is more, by a factor of up to about 10, than would in reality be registered by genuine single-line cameras. Nevertheless, only a hint of the chlorine line can be seen, even though the lines of the other constituents continue to be clearly visible. Moreover, in the upper spectrum the statistics are better. The comparison also shows, however, a greater line width in the upper spectrum which, on the one hand, is due to aberration of the spectrometer SP (without flat-field arrangement) and, on the other hand, to averaging across plasma regions having different densities. As can be seen, this does not constitute any limitation for the method at the 837.6 nm chlorine line.

The curves I and II were recorded and analyzed with a memory depth of 8 bits.

The method and the arrangement in the embodiments described were employed with surprisingly good results (down to a chlorine content of 0.5%!) for quantitative spectral analysis of chlorine, and they can likewise be used advantageously for quantitative determination of the other halogens: bromine, fluorine and iodine. The wavelength ranges of the spectral lines for the other halogens can be gathered in a similar manner (visible-light region or IR region, see above, and not masked by other strong spectral lines) from appropriate tables of spectral lines, and the most suitable spectral line ranges of these can be determined in practical experiments.

The method and the arrangements are advantageously suitable for the determination of chlorine in any type of nonmetallic or at most partially metallic material, especially in plastics. The determination of chlorine is particularly necessary in vinyl-containing materials (PVC etc), since these materials are separated, for example, in the process of recycling. The chlorine content is highly detrimental, on the grounds of corrosion, even with recyclable plastics which are to be processed, for example, by injection-molding.

With flame-proof materials, too, the method and the arrangements can be used advantageously owing to the bromine content of these materials, which is likewise problematic when they are recycled. Moreover, recyclable plastics are also known for which the determination of fluorine and iodine is important and advantageous.

The method of laser-induced spectral analysis is modified in such a way that it can be used for the analysis of halogens in materials. This is achieved by a plasma being generated, by means of a high-energy laser, on the object to be analyzed and the luminous intensity of a plasma volume slice element whose size and orientation are freely definable, being employed, in combination with a spectrometer and a two-dimensional image recording system whose sensitivity, triggerability and gate opening time are adjustable, for analytical purposes. Averaging over the relatively large volume, over a range of the density gradients and temperature gradients increases the sensitivity and reproducibility (compared with customary one-dimensional detection methods) which crucially enable the analysis of halogens.

We claim:

1. A method for spectral analysis by means of laser emission of non-metallic or at most partially metallic materials containing halogen, in particular chlorine, a pulsed laser beam (P) being directed at the material (T) to generate a plasma (PA) and the light emitted by the plasma in an expansion direction in conical form being focussed optically, being passed to a spectrometer (SP) and being analyzed after a predefined delay after the pulsed laser beam (P) has been triggered, and the pulsed laser beam (P) having an energy density between about $10^8$ and about $10^{12}$ W/cm$^2$, wherein averaging is carried out temporally and spatially over a range of density gradients and temperature gradients of the plasma (PA) in order to obtain stable, reproducible and high-luminosity spectral line information for analysis, by means of all of the luminous intensities emanating from at least one volume slice (V) of the expansion cone being summed and averaged.

2. A method as claimed in claim 1, wherein a conical section volume slice (V) is selected which is oriented perpendicularly to the expansion direction of the plasma (PA) and which is generated by a single pulsed laser beam (P) (laser shot).

3. A method as claimed in claim 1, wherein a volume slice is selected which is oriented in the direction of the expansion of the plasma (PA) and which is generated by a single pulsed laser beam (P) (laser shot).

4. A method as claimed in claim 1, wherein the expansion cone is projected onto the entrance slit (SL) of the spectrometer (SP), the spectrometer slit (SL) cuts out a volume slice (V), and the spectrally resolved light emission of the volume slice (V), having passed through the spectrometer (SP), is detected two-dimensionally by a matrix-type image recorder (BA).

5. A method as claimed in claim 1, wherein the luminous intensity is averaged and analyzed over a time window of at least 100 ns after the predefined delay has elapsed.

6. A method as claimed in claim 1, wherein the mean focal distance (e) between the nonmetallic or partially metallic material and the volume slice (V) is from about 3 to about 6 mm.

7. A method as claimed in claim 1, wherein in the case of chlorine the predefined delay is 4 µs or less with respect to the plasma (PA) being produced.

8. A method as claimed in claim 1, wherein the pulsed laser beam (P) has a Gaussian distribution which is generated by a laser (L) operated in $TEM_{00}$ mode.

9. A method as claimed in claim 4, wherein the matrix-type image recorder (BA) is a CCD camera (CCD) comprising a chip having at least 10 rows, in particular a chip having about 500 to 600 rows, the luminous intensity being detected along the longitudinal direction of the slit (SL) in the rows and the spectral resolution (wavelength) being detected in the columns of the matrix or vice versa.

10. A method as claimed in claim 4, wherein downstream of the matrix-type image recorder (BA) there is connected a digital analysis unit (DM) having a memory depth of at least 4 bits and having at least 10 rows and the number of columns of the corresponding base width of the spectral line to be analyzed, ie. with about 200 memory locations.

11. A method as claimed in claim 1, wherein the plasma (PA) produced of the expansion cone is postexcited by means of an additional transverse electric discharge spark gap (B) and the light emitted thereupon is passed to the spectrometer (SP).

12. A method as claimed in claim 1, wherein for the purpose of the chlorine analyses the spectral lines in the wavelength region from about 480 nm to about 550 nm, in particular at about 480, 490, 500, 510, 520, 530, 540–550 nm or at about 838 nm or at about 859 nm are used.

13. A method as claimed in claim 1, wherein a plurality of spectral ranges are recorded either simultaneously via parallel recording channels or consecutively, and only sub-ranges thereof are subjected to further analysis.

14. An arrangement for carrying out the laser emission spectral analysis as claimed in claim 1, comprising a pulsed laser (L) having an energy density between about $10^8$ and about $10^{12}$ W/cm$^2$, whose pulsed laser beam (P) is directed at the nonmetallic or at most partially metallic material (T), an optically focussing apparatus (LE), which directs and colimates the light emitted by the plasma (PA) to the slit (SL) of a spectrometer (SP), a matrix-type image recorder (BA) by means of which the intensity of the volume slice (V), projected via the spectrometer slit (SL), of the emitted light after it has passed through the spectrometer (SP) is spectrally resolved and can be summed, temporally and spatially, by means of an image storage device and analysis device (BS and DM), and a control device (SC) between the laser (L), the spectrometer (SP), the image recorder (BA) and the image storage device and analysis device, (BS and DM) for correct storage and analysis, in terms of time intervals, of the spectral signals of the emitted light.

15. An arrangement as claimed in claim 14, comprising an analysis device (DM) which contains digital logic units to which the spectral signals stored in the image memory (BS) are passed.

16. An arrangement as claimed in claim 14, wherein the matrix-type image recorder (BA) is a CCD camera (CCD) having at least 10, in particular about 500 or about 600 rows and as many columns.

17. An arrangement as claimed in claim 14, comprising a postexcitation device which comprises a triggered spark gap (B) having Cu electrodes, a voltage of about 5 kV, a capacitance of about 2 mF and an inductance of about 100 mH.

18. An arrangement as claimed in claim 16, wherein there is connected, upstream of the image recorder (BA), an image amplifier (BV) which can be controlled temporally, in terms of a gate and delay time, with a resolution of up to about 10 ns, in order to generate a time window of at least 100 ns and to set a delay time of about 4 ms.

19. An arrangement as claimed in claim 14, wherein the spectrometer (SP) comprises image-field correcting elements (flat-field apparatus).

20. An arrangement as claimed in claim 14, wherein the pulsed laser is operated in $TEM_{00}$ mode.

21. An arrangement as claimed in claim 14, wherein the imaging optics (LE, FL) used of the plasma comprise an achromat.

22. An arrangement as claimed in claim 14, wherein the imaging optics used of the plasma comprise zoom optics (FL) for variable setting of the working distance (e) and the linear magnification.

23. An arrangement as claimed in claim 13, wherein, for the purpose of images being formed in two steps, two cylindrical lenses (FL) connected in series are provided, which form images in the y and z direction, it thus being possible, e.g., for the size of the plasma volume which is to be studied to be individually defined in the y and z direction.

* * * * *